(12) United States Patent
Eckhardt

(10) Patent No.: US 6,461,568 B1
(45) Date of Patent: Oct. 8, 2002

(54) METHOD AND APPARATUS FOR STERILIZING SMALL OBJECTS

(75) Inventor: Richard A. Eckhardt, Arlington, MA (US)

(73) Assignee: UV-Solutions, LLC, Wellesley, MA (US)

( * ) Notice: Subject to any disclaimer, the term of this patent is extended or adjusted under 35 U.S.C. 154(b) by 0 days.

(21) Appl. No.: 09/469,043

(22) Filed: Dec. 21, 1999

Related U.S. Application Data
(60) Provisional application No. 60/113,770, filed on Dec. 23, 1998.

(51) Int. Cl.[7] .................................................. A61L 9/00
(52) U.S. Cl. ..................... 422/24; 250/455.11; 422/22
(58) Field of Search ................. 422/22, 24; 250/455.11

(56) References Cited

U.S. PATENT DOCUMENTS

| | | | |
|---|---|---|---|
| 4,239,041 A | 12/1980 | Popovich et al. | |
| 4,464,336 A | 8/1984 | Hiramoto | 422/24 |
| 4,469,835 A | 9/1984 | Lauria | |
| 4,475,900 A | 10/1984 | Popovich et al. | |

(List continued on next page.)

FOREIGN PATENT DOCUMENTS

| | | |
|---|---|---|
| EP | 0925793 A2 | 6/1999 |
| EP | 1 033 138 A1 | 9/2000 |
| FR | 2492665 A | 4/1982 |
| GB | 2301272 A | 11/1996 |

OTHER PUBLICATIONS

"Derma–Wand Germicidal UVC Lamp", National Biological Corporation, Form No. DW–1, Dec. 1998.
ROVA UV TOOTHBRUSH STERILIZER for Homeuse, for a New Sanitary Life, RD–930 Toothbrush Sterilizer Ultraviolet (UV), RoadPia Brand! pp. 1–2, Jei Corporation, printed Feb. 27, 2000.
Test Result RD–930 RoadPia UV Toothbrush Sterilizer, pp. 1–2, Jei Corporation, printed Feb. 27, 2000.
International Search Report dated Apr. 12, 2000.

*Primary Examiner*—Krisanne Thornton
(74) *Attorney, Agent, or Firm*—Wolf, Greenfield & Sacks, P.C.

(57) ABSTRACT

Methods and apparatus for sterilizing small objects. A small object is inserted into a chamber formed in the sterilizer. A portion of the small object mates with a lockout device to disable the lockout device. After the lockout device is disabled, the sterilizer produces at least one flash of high intensity ultraviolet light produced by an ultraviolet light source. The ultraviolet light flash kills microorganisms on the surface of the small object. The chamber of the sterilizer may be lined with a reflective coating to disperse the ultraviolet light around the chamber so that most, if not all, of the small object within the sterilizer is exposed to the ultraviolet light.

13 Claims, 7 Drawing Sheets

U.S. PATENT DOCUMENTS

| | | | |
|---|---|---|---|
| 4,503,333 A | 3/1985 | Kulin et al. | |
| 4,620,845 A | 11/1986 | Popovich et al. | |
| 4,806,770 A | 2/1989 | Hylton et al. | 250/455.1 |
| 4,868,397 A * | 9/1989 | Tittel | 250/455.1 |
| 4,877,964 A | 10/1989 | Tanaka et al. | |
| 4,910,942 A | 3/1990 | Dunn et al. | 53/425 |
| 4,950,902 A | 8/1990 | Ritter | 250/455.1 |
| 4,952,369 A | 8/1990 | Belilos | 422/24 |
| 4,973,847 A | 11/1990 | Lackey et al. | 250/455.1 |
| 5,023,460 A | 6/1991 | Foster, Jr. et al. | 250/455.1 |
| 5,126,572 A * | 6/1992 | Chu | 250/455.11 |
| 5,144,146 A | 9/1992 | Wekhof | 250/492.1 |
| 5,185,532 A | 2/1993 | Zabsky et al. | 250/455.11 |
| 5,260,020 A | 11/1993 | Wilk et al. | |
| 5,597,597 A | 1/1997 | Newman | |
| 5,607,419 A | 3/1997 | Amplatz et al. | |
| 5,614,151 A | 3/1997 | LeVay et al. | 422/24 |
| 5,637,877 A * | 6/1997 | Sinofsky | 250/492.1 |
| 5,671,314 A | 9/1997 | Gregory et al. | |
| 5,695,482 A | 12/1997 | Kaldany | |
| 5,786,598 A | 7/1998 | Clark et al. | 250/455.11 |
| 5,788,940 A | 8/1998 | Cicha et al. | |
| 5,892,233 A | 4/1999 | Clement | 250/455.11 |
| 5,898,277 A | 4/1999 | Farnsworth et al. | |
| 5,920,075 A | 7/1999 | Whitehead | 250/492.1 |
| 5,925,885 A | 7/1999 | Clark et al. | 250/492.1 |
| 5,996,155 A | 12/1999 | Chao et al. | |
| 6,087,781 A | 7/2000 | Leppelmeier | |
| 6,090,346 A | 7/2000 | Rose et al. | |
| 6,132,784 A | 10/2000 | Brandt et al. | |
| 6,297,047 B1 | 10/2001 | Butts | |

* cited by examiner

METHOD AND APPARATUS FOR STERILIZING SMALL OBJECTS

This application claims the benefit of provisional application Ser. No. 60/113,770, filed Dec. 23, 1998.

BACKGROUND

A number of small objects used in everyday life can serve as a transport mechanism for disease causing microorganisms. Objects that are handled or breathed-on by different people, or come in contact with surfaces contaminated by other people or animals, can themselves become contaminated. If these objects then contact a person's mouth, nose, eyes, other body orifice, or area of damaged skin, they can transmit diseases to the person or cause infection.

This contamination problem is particularly acute with objects used by infants, as they have a propensity to place small objects in their mouth, or touch larger ones with their mouth. Some devices used by infants are designed to be placed in the infant's mouth, such as bottle nipples, pacifiers, teething rings, etc. As these devices are often dropped by the infant onto contaminated surfaces, such as the floor, it is desirable to have a quick and easy method to sterilize them before returning them to the infant. A traditional approach to sterilizing such objects was to place them in boiling water.

Other objects used by both adults and children, such as toothbrushes, contact lens, combs, hairbrushes, eating and drinking utensils, medical and dental devices, etc., also may need to be sterilized in order to reduce the possibility of disease or infection from the use of such objects.

One approach to sterilizing objects is to expose the object to continuous stream of ultraviolet (UV) light produced by a sterilizing lamp. Systems that implemented this approach typically required some source of external power, such as a connection to a wall socket, to drive the lamp for long periods of time. This required connection typically made these systems non-portable. In addition, if such systems are used near a sink (for instance, for sterilizing a toothbrush), electrical shock or electrocution is possible.

SUMMARY

Various embodiments of the present invention are directed to methods and apparatus for sterilizing small objects. The methods and apparatus utilize a flash of ultraviolet light from an ultraviolet light source to sterilize the small object. In some embodiments, a portion of the small object serves to disable a lockout device and enable a sterilizer to operate.

In one embodiment of the present invention, a portable sterilizer for sterilizing a small object is disclosed. The portable sterilizer of this embodiment includes a housing having walls defining a chamber within the housing for receiving a portion of the small object. The portable sterilizer also includes an ultraviolet light source disposed within the housing so that ultraviolet light emitted from the ultraviolet light source may enter the chamber. In addition, this embodiment includes a battery receiver configured to receive a at least one battery and control electronics connected between the battery receiver and the ultraviolet light source that is configured to deliver at least one energy pulse to the ultraviolet light source so that the ultraviolet light source produces a flash of ultraviolet light. The portable sterilizer of this embodiment also includes a lockout device that disables operation of the sterilizer unless the portion of the small object has been placed within the chamber.

In another embodiment of the present invention, a small object for use with a portable sterilizer is disclosed. The small object of this embodiment includes a first end to be inserted into a portable sterilizer and a mating feature configured to disable a lockout device of a portable sterilizer.

In yet another embodiment of the present invention, a method of sterilizing a small object is disclosed. The method of this embodiment includes a step of placing at least a portion of the object in a sterilizer such that a lockout device of the sterilizer is disabled. The method of this embodiment also includes exposing the portion of the small object in the sterilizer to a flash of ultraviolet light.

BRIEF DESCRIPTION OF THE DRAWINGS

Various embodiments of the invention are illustrated and described below with reference to the accompanying drawings, in which like items are identified by the same reference designation, wherein.

DETAILED DESCRIPTION

Figure 1:
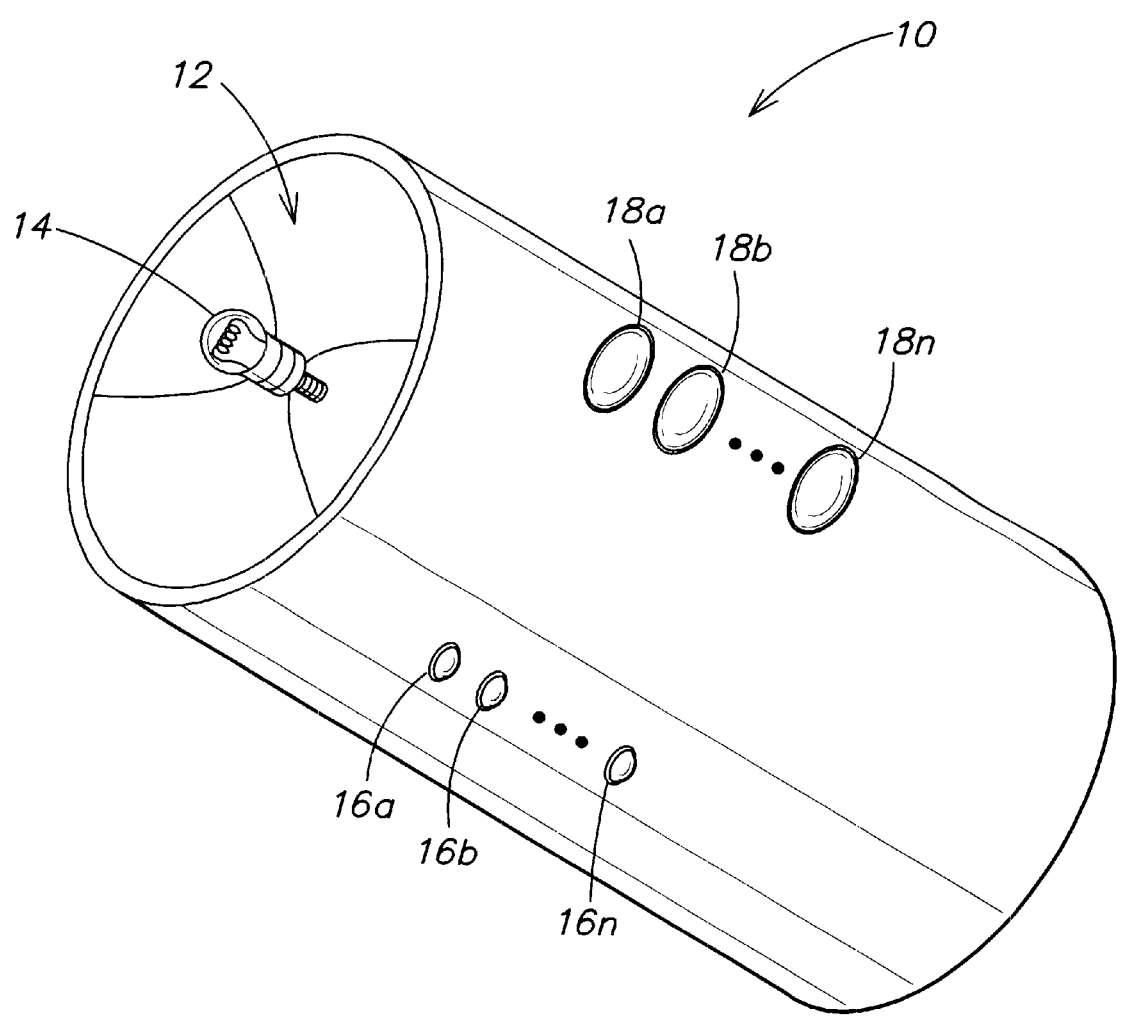
FIG. 1 is a example of an embodiment of a portable sterilizer.

FIG. 1 is a example of an embodiment of a portable sterilizer 10. The sterilizer 10 of this embodiment receives a small object (or a portion thereof) such as a pacifier, toothbrush or drinking cup, into a chamber 12. The sterilizer 10 sterilizes the small object by exposing the it to a flash of ultraviolet light from an ultraviolet light source 14. In some embodiments, the sterilizer may produce more than one flash of ultraviolet light. The term "flash" as used herein with respect to the ultraviolet light source 14 means that the ultraviolet light source is not continuously operated for longer than about 1 second. In some embodiments, the ultraviolet light source 14 may not be continuously operated for longer than about 0.5 seconds per flash. In other embodiments the ultraviolet light source 14 may operate for less than about 100 milliseconds.

The ultraviolet light source 14 may be, for example, a high intensity flash lamp such as a xenon strobe light. Ultraviolet light having a wavelength in the range of 160 to 300 nanometers may be lethal to some microorganisms and is therefore effective for sterilizing objects. A total exposure of about 10 milliwatt-seconds of ultraviolet light energy per square centimeter is sufficient to effectively disinfect most surfaces of small objects such as a pacifier, bottle nipple, toothbrush or drinking cup. The amount of ultraviolet light energy to sterilize an object is dependent on characteristics of the surface and the environmental conditions, such as the temperature because exposing the object's surface to ultraviolet light raises its temperature and impacts the effectiveness of the ultraviolet light sterilization.

Xenon strobe lamps normally produce light across the spectrum of wavelengths from 160 to 2000 nanometers. For many applications of the xenon strobe, ultraviolet light with a wavelength of less than 380 nanometers is not desired, so the typical glass envelope around the xenon gas is designed to stop the light having a wavelength less than 380 nanometers. In one embodiment, a xenon lamp with ultraviolet light transmitting glass may be used to maximize the output of the sterilizing ultraviolet light. In one embodiment, the envelope may be made of quartz.

The ultraviolet light and the light emitted in the visible and infrared range (380 to 2000 nanometers) provides energy for instantaneous heating of the surface of the object to be sterilized for more effective sterilization in a short time. This short impulse of radiant energy heats the surface of the object rapidly, but typically does not heat the interior of the object. The impulse of radiant energy uses far less energy than heating the entire object and will have less effect on the structural integrity of the object such as would be caused by the melting of plastic.

Using this "flash" technique, small objects such as a pacifier or bottle nipple could be sterilized with a total power to the ultraviolet light source 14 in the range of 1 to 20 joules. Xenon flash lamps which operate at higher current density in the xenon gas, produce a higher percentage of the output light in the ultraviolet spectrum (a wavelength of 160 to 380 nanometers) for more efficient operation in the sterilizer application. An example of such a flash lamp is a xenon short-arc lamp.

Alternatively, the ultraviolet light source 14 could provide continuous ultraviolet light with a wavelengths in the range of 160 to 380 nanometers. This continuous technique would provide continuous radiant heating of the object that would result in a smaller temperature gradient between the surface and interior of the object and a lower surface temperature and therefore less benefit from the heating.

In some embodiments, the sterilizer includes a lockout device (not shown) that is disabled if a portion of the small object is placed in the chamber 12. If the lockout device is disabled, the sterilizer 10 may be operated (either automatically or by user controls). In some embodiments, the lockout device may not be disabled unless the object has formed a seal around the edge of the chamber 12 so that ultraviolet light cannot escape from the chamber 12. Sealing the ultraviolet light may reduce a user's exposure to, and avoid the possibility of injury from, the high intensity ultraviolet light produced by the ultraviolet light source 14. Of course, the light seal may be created by a different portion of the small object than disables the lockout device.

The lockout device can be implemented in several different manners. For example, a projection on a pacifier flange or baby bottle cap may activate a mechanical or optical switch in the sterilizer 10 to disable as the lockout device. Alternatively, a magnet in the pacifier or baby bottle cap may be sensed by a sensor in the sterilizer 10, and, if the magnet has been sensed, the lockout device is disabled. In some embodiments, the lockout switch may be the control switch for operating the sterilizer 10. If the lockout switch is the control switch for operating the sterilizer 10, the act of inserting the object to be sterilized and, thus, disabling the lockout device, would initiate operation of the sterilizer 10.

The sterilizer 10 may also include user indication lights 16a, 16b, . . . 16n. These user indication lights convey information about the sterilizer 10 the a user. For instance, light 16a could indicate that that the sterilizer 10 is on, light 16b could indicate that the sterilizer 10 is charged and ready to operate, and light 16n could indicate that the lockout device has been disabled and thus, that the sterilize 10 may operate. Many other user indicators may be present if other information is desired to be conveyed to the user, such as the amount of power remaining in the battery.

The sterilizer 10 may also include several user operation buttons 18a, 18b, . . . 18n. These user operation buttons provide the user with the ability to control the operation of the sterilizer 10. However, the sterilizer 10 may operate automatically after the lockout device has been disabled without using these buttons. The user operation buttons may control, for example, the charging of the sterilizer 10 and whether the sterilizer 10 is turned on.

Figure 2:
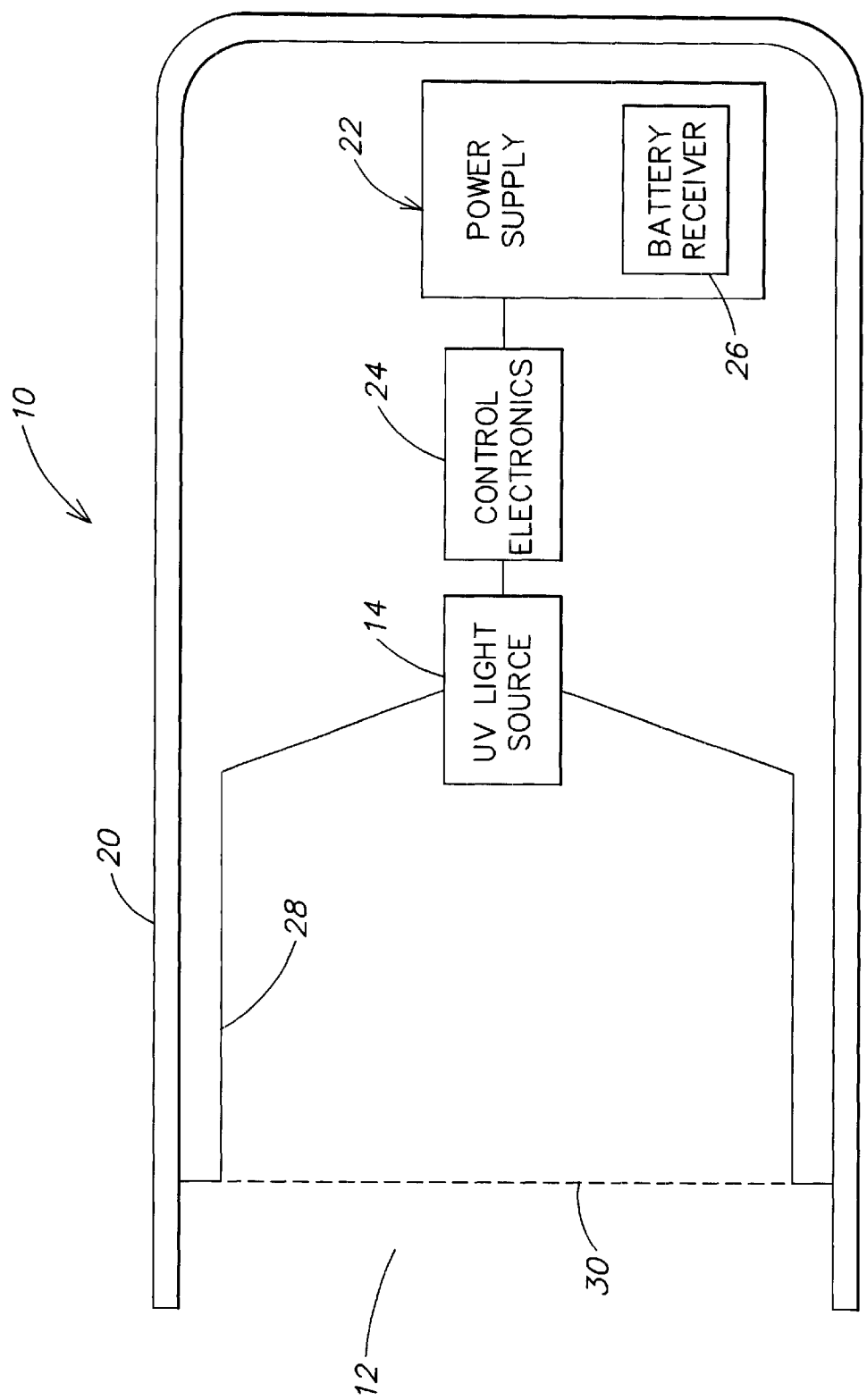
FIG. 2 shows a simplified cross-sectional cutaway view of an embodiment of a portable sterilizer.

FIG. 2 shows a simplified cross-sectional cutaway view of an embodiment of a portable sterilizer 10. The sterilizer 10 includes an outer housing 20 which defines the outer boundaries of the sterilizer. The outer housing 20 could be formed of metal, plastic of any other material suitable for use with hand-held electronic devices. The outer housing 20 is formed such that a chamber 12 for receiving objects (or portions thereof) to be sterilized is created. The sterilizer 10 may also include an ultraviolet light source 14 within the housing 20 which is positioned so that it may provide ultraviolet light to the chamber 12 if the ultraviolet light source 14 is illuminated. The sterilizer 10 may also include a power supply 22 and control electronics 24 which, in combination, provide electrical energy to the ultraviolet light source 12. The electrical energy causes the ultraviolet light source 12 to produce the flash discharge which sterilizes the object. The power supply 22 may be a battery such as a 3V lithium battery or one or more AA batteries, and the like. Accordingly, the power supply 22 may include a battery receiver 26 within the outer housing 20 to hold the batteries that may be used as a source of power.

The portable sterilizer 10 is effective for sterilizing small objects such as, for example, a pacifier, toothbrush or drinking cup. In general, the sterilizer 10 produces at least one flash of ultraviolet light from the ultraviolet light source 14 if a small object is placed in the chamber 12. The flash of ultraviolet light sterilizes any small object (or portion thereof) that is placed within the chamber 12. As discussed below, the small object itself may include portions that mate with the sterilizer 10 to enable the operation of the sterilizer 10.

In one embodiment, the chamber 12 may have a reflective 28 coating disposed on at least a portion thereof. The reflective coating causes the ultraviolet light to be dispersed around the chamber 12 and, thus, assures that the light from the ultraviolet light source 14 reaches the entire surface of the portion of the object that is within the chamber 12. The reflective material could be a mirror, aluminum foil, or any other material that reflects light.

In FIG. 2, the lockout device shown by the dashed line labeled with reference numeral 30. The dashed line indicates that the lockout device 30 serves as a check that the open end of the chamber 12 is covered (i.e., a light seal is made) before the sterilizer will work. As discussed with respect to FIGS. 3–4C, a portion of the small object itself may serve to disable the lockout device 30 and enable the operation of the sterilizer. That is, the small object includes a mating feature designed to mate with and disable the lockout device 30 of the sterilizer 10. Of course, the light may be sealed by one portion of the small object and the lockout device 30 disabled by another portion of the small object.

Figure 3:
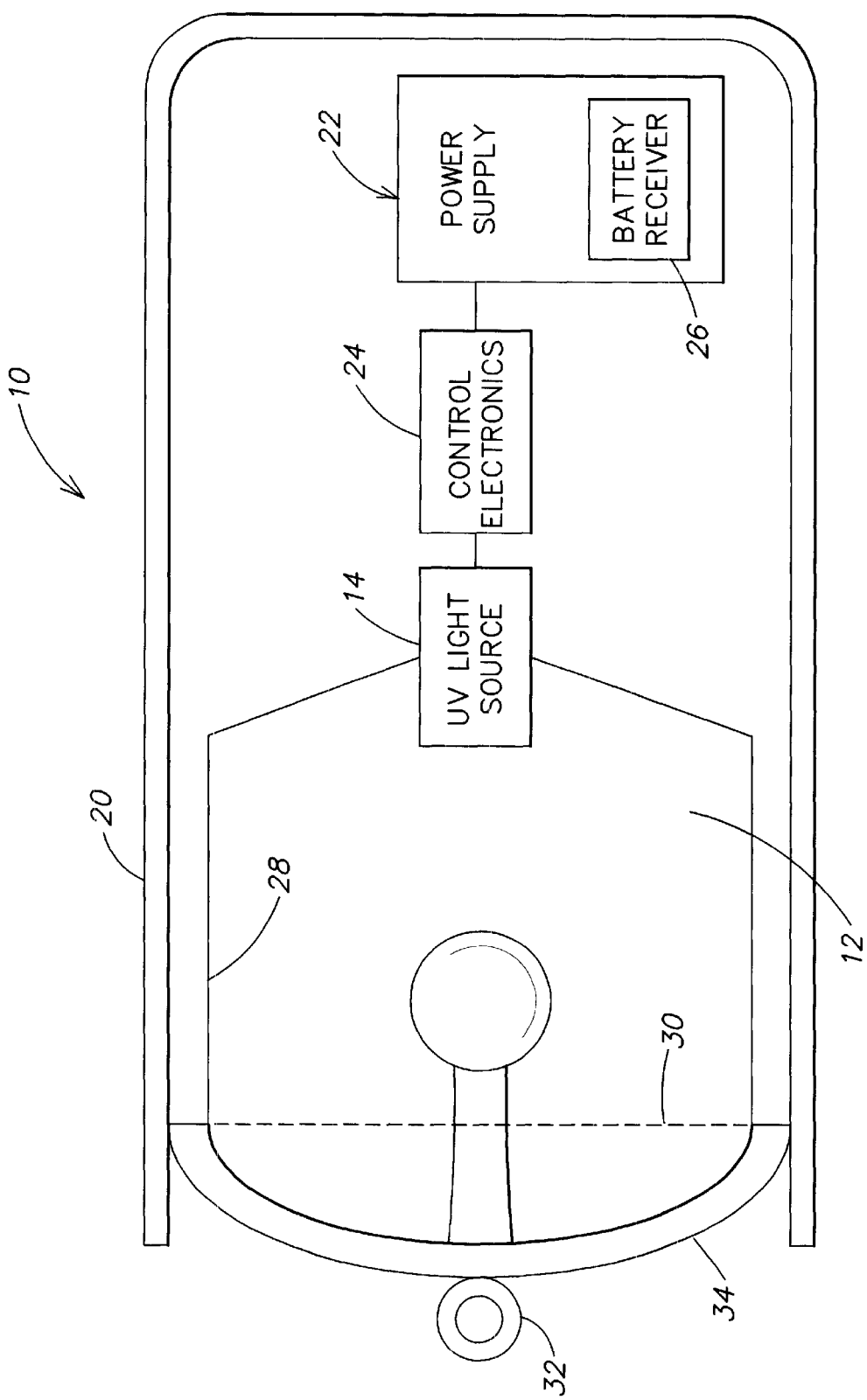
FIG. 3 shows a cross-sectional side view of an example of a sterilizer having a pacifier inserted therein for sterilization.

FIG. 3 shows a cross-sectional side view of an example of a sterilizer 10 having a pacifier 32 inserted therein for sterilization. However, other small objects may be sterilized by the sterilizer 10, such as a toothbrush or drinking cup. The open end of the chamber 12 may be sized so that it matches the shape of the flange 34 of the pacifier. In this embodiment, the lockout device 30 mates with the flange 34. That is, the lockout device 30 is constructed so that its shape is congruent with the shape of the flange 34 and is disabled if the flange is mated with the lockout device 30. Thus, a portion of the pacifier 32 itself (e.g., the flange 34) serves to seal light in the sterilizer 10 to keep a user from being exposed to the ultraviolet light as well serving to enable the operation of the sterilizer 10 by disabling the lockout device 30.

Small objects such as pacifiers, bottle nipples, toothbrushes and drinking cups are typically may of plastic or organic materials. Many plastic polymers and natural organic materials are adversely affected by exposure to ultraviolet light. To overcome this problem, the materials used in the objects to be sterilized could include ultraviolet light stabilizers. The stabilizers are standard plastics additives that have been developed to increase the useful life of plastic exposed to ultraviolet light, such as in applications where the plastic is exposed to direct sunlight. Alternatively, the plastic materials used could be made opaque to ultraviolet light (or all light) such as through the addition of dark colorants. For example, black plastics are typically colored using carbon particles which are opaque to all light, including ultraviolet. The carbon particles keep the light from penetrating into the plastic and protect the bulk of the plastic from damage due to ultraviolet light exposure.

Figure 4A:
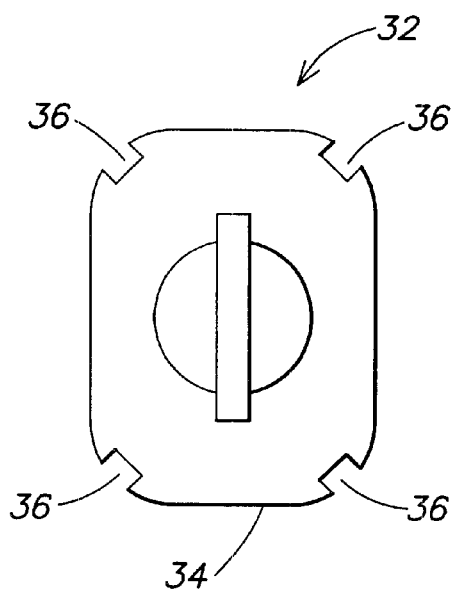
FIG. 4A shows an end view of a pacifier having a flange designed to mate with a lockout device.

FIG. 4A shows an end view of a pacifier 30 having a flange 32 designed to mate with a lockout device (not shown). In this embodiment, the flange 32 includes a plurality notches 34 that accept portions of a lockout device on the sterilizer 10. In this example, the lockout device on the sterilizer 10 may include four projections above a pressure sensitive ring or a plurality of pressure sensitive switches. The projections slide through the notches 34 and allow the fiance 32 to exert pressure on the ring or switches in order to disable the lockout device. As discussed above, the lockout device may be implemented in a variety of ways and, in one embodiment, a portion of the object being sterilized serves to disable the lockout device.

Figure 4B:
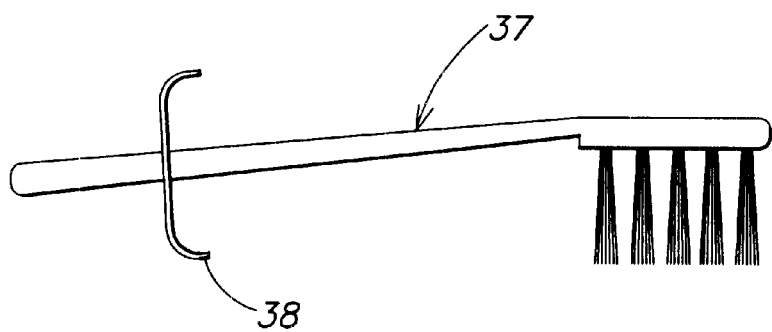
FIG. 4B shows a side view of a toothbrush.

FIG. 4B shows a side view of a toothbrush 37. The toothbrush 37 is substantially similar to almost any toothbrush commercially available. However, the toothbrush 37 also includes a flange 38 mounted on the handle. Similar to the flange on the pacifier described above, this flange 38 is designed to disable a lockout device on a portable sterilizer. In addition, the flange 38 serves to form a light seal for the chamber. The flange 38 could have additional features that disable the lockout device. For instance, the flange 38 could include notches similar to those described above with respect to the pacifier.

Figure 4C:
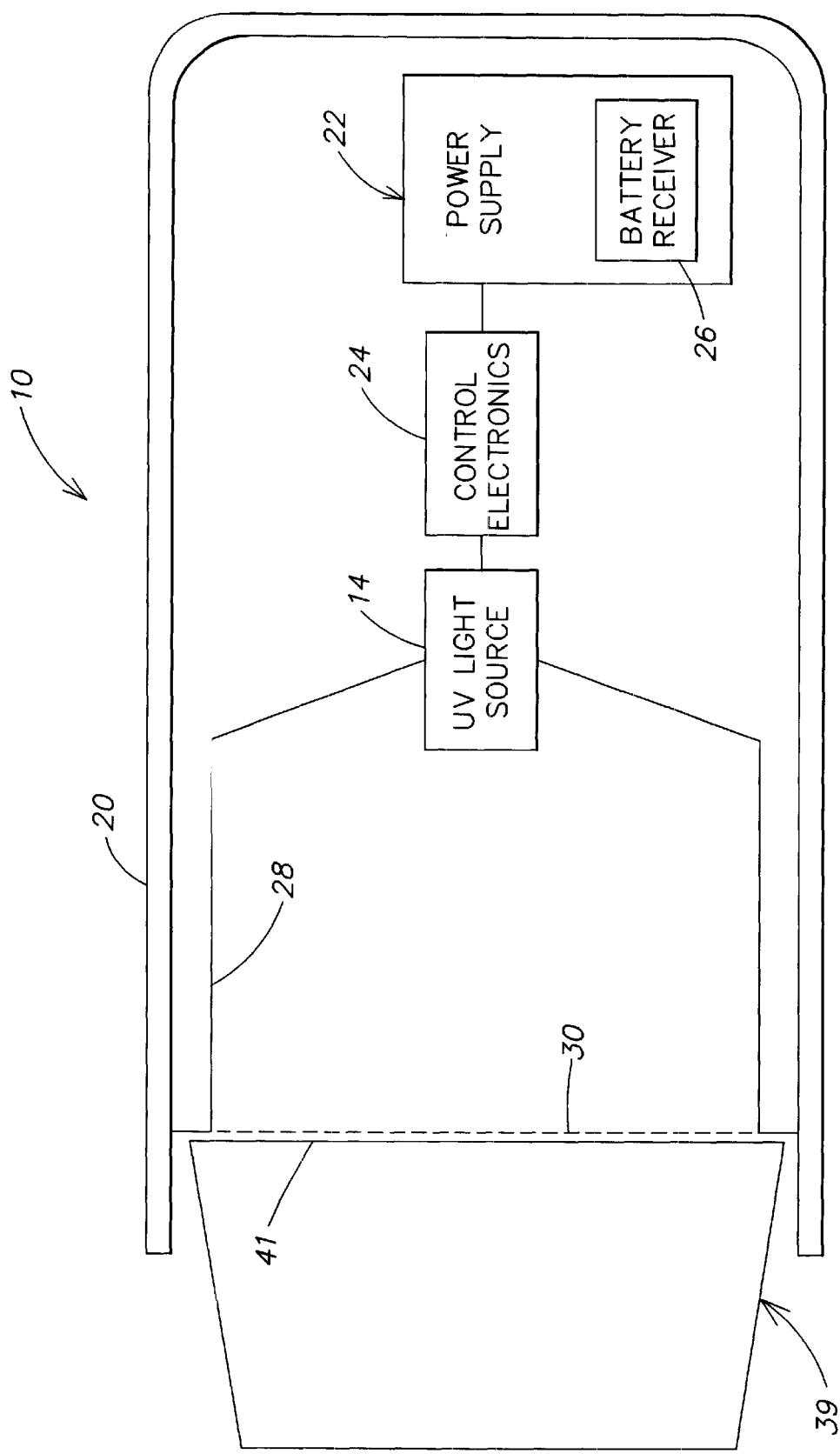
FIG. 4C is a cutaway side view of portable sterilizer which has a drinking cup inserted therein.

FIG. 4C is a cutaway side view of portable sterilizer 10 which has a drinking cup 39 inserted therein. The drinking cup includes a top rim 41 that engages with and disables the lockout device 30 to allow the sterilizer 10 to operate. The flash of ultraviolet light from the ultraviolet light source 14 enters and sterilizes the interior portions of the drinking cup 39. It should be understood that the drinking cup 39 could have additional features beyond just the shape itself that disable the lockout device. For instance, the drinking cup 39 could include notches similar to those described above with respect to the pacifier.

All of the proceeding examples of small objects that may be sterilized is not limited. That is, the teachings herein apply to any object that has portion that is capable of disabling the lockout device of a sterilizer. Although a few examples of portions of a small object that may disable a lockout device have been disclosed, one of ordinary skill will realize that a multitude of mating features exist such as, for example, a flange, projections extending from the small object that mate with the sterilizer 10, and the like.

Figure 5:
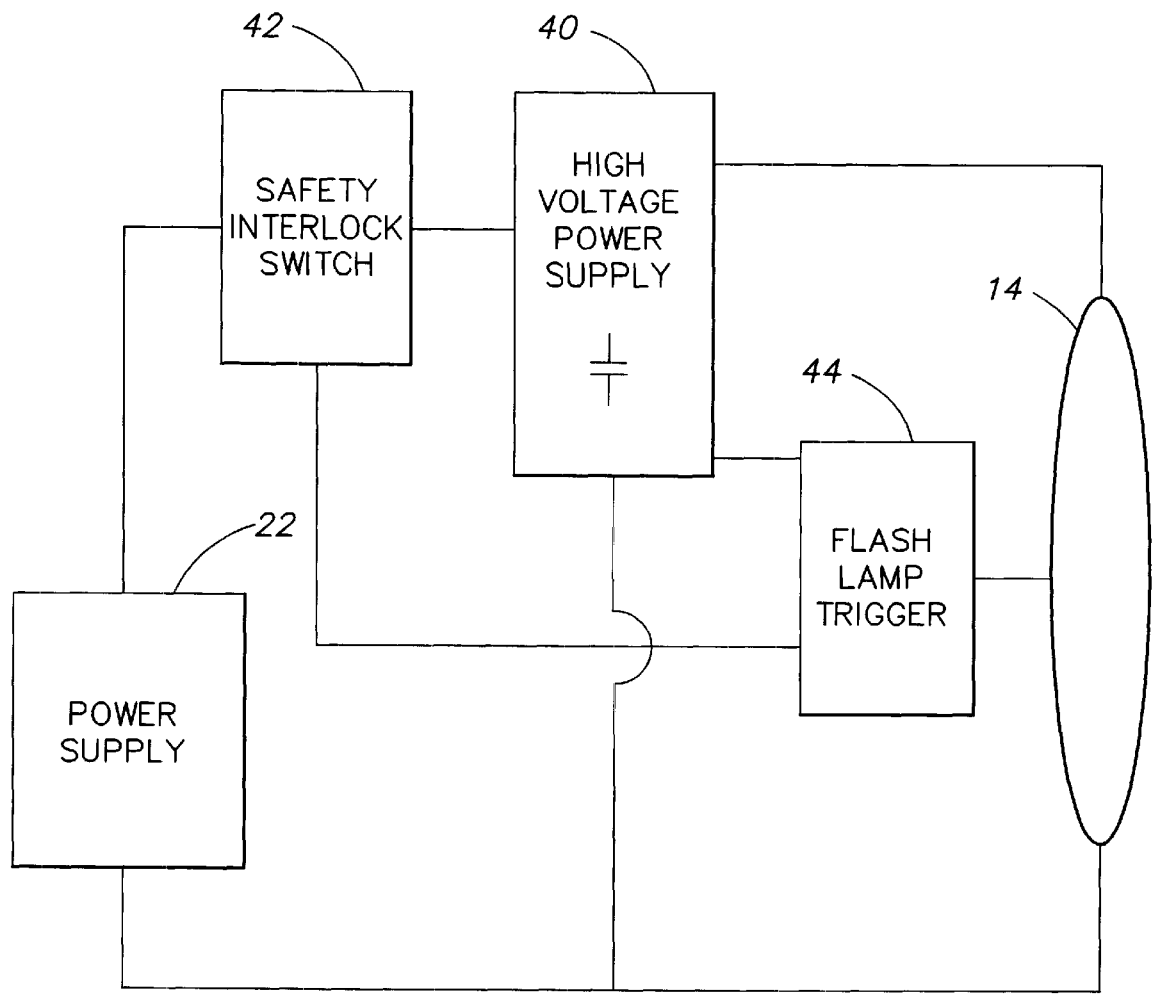
FIG. 5 is a block diagram of one embodiment of the control electronics including the power supply.

FIG. 5 is a block diagram of one embodiment of the control electronics 20 including the power supply 18. Generally, the control electronics 20 utilizes a high voltage power supply 40 that contains a capacitor to store the energy that powers the ultraviolet light source 14. For simplicity, the ultraviolet light source 14 is referred to as a flash lamp in this example. The high voltage produced by the high voltage power supply 40 is typically in the range of 200V to 1000V depending characteristics of the flash lamp used. Small linear flash lamps typically operate with voltages of 200V to 500V and small short-arc flash lamps may operate with voltages of 1000V or more. The voltage is selected based on the specification of the flash lamp 14 that is used, the total energy desired per flash, and the maximum flash current desired. A higher voltage will provide a higher flash current for the same energy, resulting in a greater percentage of the flash light output in the ultraviolet spectrum.

The high voltage power supply 40 in the sterilizer 10 is electrically connected to the power supply 18 by a safety interlock switch 42. The safety interlock switch 42 is operated by the lockout device 30 (FIG. 2) and allows the power supply 22 to provide power to the high voltage power supply 40 if the lockout device 30 disabled. Thus, the safety interlock switch 42 prevents the sterilizer 10 from operating if the sterilizing compartment (e.g., the chamber) is open.

The energy per flash, in joules, is determined by the equation: $\frac{1}{2} CV^2$, where C is the value of the energy storage capacitor in Farads and V is the voltage in volts. For the sterilizer application, the selected voltage should be as high as possible for the particular flash lamp to produce the greatest amount of ultraviolet light. The value of the capacitor in the high voltage power supply 40 is then chosen to provide the desired amount of energy per flash. The total energy for this application will typically be in the range of 1 to 20 joules for small objects such as a pacifier or baby bottle top with nipple. The energy requirement is a function of how efficiently the light from the flash lamp 14 is directed to the object to be sterilized, the size and surface characteristics of the object, and the spectrum of the light from the flash lamp 12. The sterilizer 10 uses the least amount of energy when it is designed to deliver the sterilizing energy in a single flash. However, sterilization can also be accomplished with multiple flashes if the total energy needed to sterilize the small object is greater than is practical for a single flash or if the surface heating due to a single flash is undesirable.

The sterilizer circuitry also includes a flash trigger circuit 44 connected to both the high voltage power supply 40 and the safety interlock switch 42. The trigger circuit 44 provides a voltage pulse typically in the range of 3 kV to 15 kV (depending on the specifications of the flash lamp) to initiate a flash of light from the flash lamp 14. The flash lamp trigger 44 may be designed to operate automatically if the voltage on the capacitor in the high voltage power supply 40 reaches the desired level. The safety interlock 42 prevents the flash lamp trigger 44 from triggering the flash lamp 12 if lockout device has not been disabled (i.e., the chamber is not sealed). In one embodiment, the high voltage power supply 40 receives an enable signal via input 41 from the user (for instance, from a button as described above) that allows the capacitor to be charged.

Figure 6:
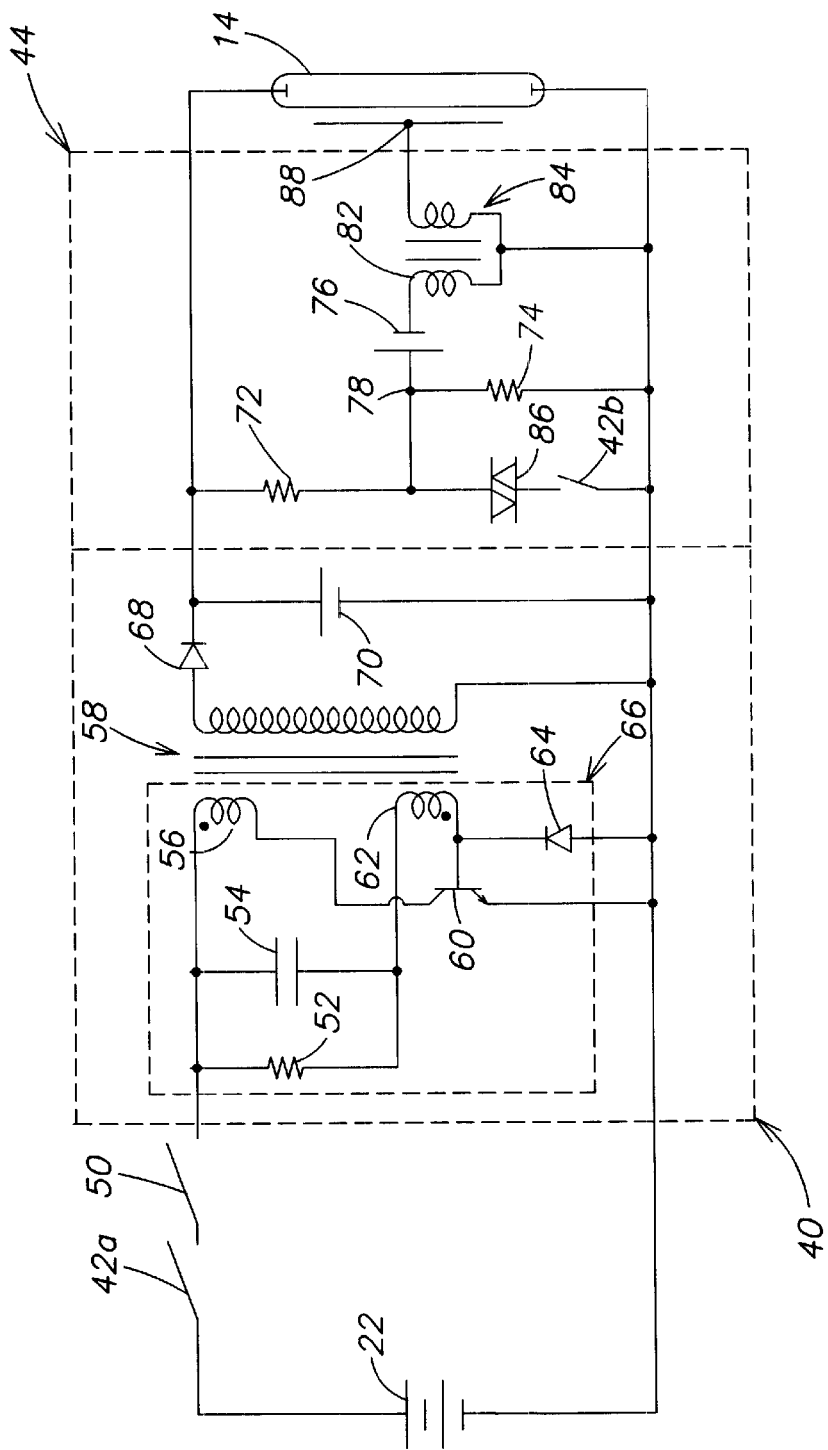
FIG. 6 shows one example of a schematic diagram of a battery powered xenon flash lamp driver circuit that may be used by a portable sterilizer in order to produce a high intensity ultraviolet light.

FIG. 6 shows one example of a schematic diagram of a battery powered xenon flash lamp driver circuit that may be used by a portable sterilizer in order to produce a high intensity ultraviolet light. For simplicity, the diagram does not show the details of the safety interlock 42 but, rather, represents the safety interlock as two switches labeled 42a and 42b. The first safety interlock switch 42a connects the high voltage power supply 40 to the power supply 22 when the lockout switch has been disabled. In some embodiments, a power switch 50 may also be included that, unless the user has activated the sterilizer, separates the high voltage power supply 40 from the power supply 22. The user may close the power switch using one of the buttons 18 (FIG. 1).

The high voltage power supply 40 includes a first resistor 52 connected in parallel with a capacitor 54 at the output side of the safety interlock switch 42a. A first side of the capacitor 54 is connected to a first side of a first input winding 56 of a high voltage transformer 58. The second side of the first input winding 56 is connected to the collector of a power transistor 60. A second side of the capacitor 54 is connected to a second side of a second input winding 62 of the high voltage transformer 58. A first side of the second input winding 62 is connected to the base of the power transistor 60. The emitter of the power transistor 60 is connected to ground. A diode 64 is connected between the base of the power transistor 60 and ground with the anode of the diode 64 connected to the base.

The combination of the first resistor 52, the capacitor 54, the first input winding 56, the second input winding 62, the power transistor 60, and the diode 64 form a low voltage oscillator 66. In one embodiment, the low voltage oscillator operates in the range of 15 to 20 kHz depending upon the values of the components.

The secondary side of the high voltage transformer 58 is connected to the anode of the high voltage diode 68. An energy storage capacitor 70 is connected in between the anode of the high voltage diode 68 and ground. Current passes through the high voltage diode 68 and charges the energy storage capacitor 70 to a voltage that drives the flash lamp 12.

The high current power source 40 is connected, as discussed above, to the flash lamp trigger 44. The second and third resistors, 72 and 74, respectively, form a series connection connected in parallel to the energy storage capacitor 70. The series connection of the second resistor 72 and the third resistor 74 form a voltage divider that charges the trigger capacitor 76 to a fraction of the voltage across the energy storage capacitor 70. The trigger capacitor 76 is coupled to node 78 between the second and third resistors, 72 and 74, respectively and a first winding 80 of the trigger transformer 82.

If the voltage across the trigger capacitor 76 reaches the threshold of the trigger diac 84 (connected between node 78 and ground), the trigger capacitor 76 is discharged through the trigger transformer 84 which creates a voltage pulse that is received by the trigger electrode (shown as node 88) on the flash lamp 14, causing it to flash using the energy stored in the energy storage capacitor 70. Without further operator controls, this example circuit would repeat this operation as long as the power switch 41 and safety interlock switches, 42a and 42b, are closed.

Suitable values for the components described above may be as follows: the first resistor 52=1 KOhm, the capacitor 54=1 µF, the energy storage capacitor 70=0.022 µF, and the second and third resistors, 72 and 74, respectively, are sized to divide the voltage such that a sufficient voltage is supplied to the trigger transformer 84 in order to trigger the flash lamp 14. As one of ordinary skill would readily realize, the above values are given by way of example only and may be varied depending upon the type of flash lamp.

The user controls (described as buttons with respect to FIG. 1) of the sterilizer that operate the power switch 41 may be a momentary switch such as a push button to initiate the sterilization cycle. The cycle would includes charging the energy storage capacitor 70 to the desired voltage, triggering the flash lamp 14, and turning off to wait for the next user start. The sterilization cycle might include more than one flash if the sterilizer is designed to require multiple flashes for sterilization. As discussed above, the control circuit could include one or more indicators, such as light emitting diodes to indicate the progress of the cycle. For some applications, the power switch 41 could be the same as the first safety interlock switch 42a. If the power switch 41 and the interlock switch 42a are the same, the cycle may start automatically when the small object is inserted and the lockout device is disabled. An additional indicator could tell the user when the cycle is completed.

An alternate configuration for the sterilizer is use a continuous output ultraviolet light as the ultraviolet light source 14, such as a mercury vapor light. The control electronics 24 type of lamp is similar to that used for fluorescent lamps, and would be constructed according to the manufacturers specifications. Typically these lamps operate in a voltage range between 100V to 300V and often require special starting circuitry to power heaters in the lamp and/or to provide a high voltage trigger to start the lamp. The operator controls and safety interlock for this circuit would similar to that for the flash lamp circuit described above.

The foregoing description of a few embodiments of the invention is merely illustrative and not limiting, having been presented by way of example only. Numerous modifications and other embodiments are within the scope of one of ordinary skill in the art and are contemplated as falling within the scope of the invention.

What is claimed is:

1. A portable sterilizer for sterilizing an object comprising:
   a housing having walls defining a chamber within the housing for receiving a portion of the object;
   an ultraviolet light source disposed within the housing so that ultraviolet light emitted from the ultraviolet light source may enter the chamber;
   a battery receiver configured to receive at least one battery;
   control electronics connected between the battery chamber and the ultraviolet light source that is configured to deliver at least one energy pulse to the ultraviolet light source so that the ultraviolet light source produces a flash of ultraviolet light;
   wherein the housing and at least a portion of the object form a seal to substantially contain the ultraviolet light; and
   a lockout device that disables operation of the light source unless the portion of the object has been placed within the chamber and the seal is substantially complete.

2. The portable sterilizer of claim 1, wherein the chamber has a reflective member disposed on at least a portion thereof.

3. The portable sterilizer of claim 1, wherein the ultraviolet light source is a flash lamp.

4. The portable sterilizer of claim 1, wherein the ultraviolet light source is a xenon strobe light.

5. The portable sterilizer of claim 1, further comprising a DC power source disposed in the battery chamber.

6. The portable sterilizer of claim 1, wherein the control electronics include a safety interlock switch connected to the lockout device.

7. The portable sterilizer of claim 6, wherein the control electronics further includes a light source power supply that includes a capacitor and is connected to the power supply through the safety interlock switch.

8. The portable sterilizer of claim 7, wherein the light source power supply provides the at least one energy pulse to the ultraviolet light source.

9. A method of sterilizing a small object comprising:

placing at least a portion of the object in a sterilizer to form an ultraviolet light containing seal; and only upon substantial completion of the seal, such that a lockout device is disabled, exposing the portion of the small object in the sterilizer to a flash of ultraviolet light.

10. The method of claim 9, wherein the exposing step comprises exposing the small object to a flash of ultraviolet light lasting less than one second.

11. The method of claim 10, wherein the exposing step comprises exposing the small object to a flash of ultraviolet light lasting less than about one-half second.

12. The method of claim 9, wherein the object is one of a pacifier, a bottle nipple, a toothbrush and a drinking cup.

13. A sterilizer/disinfector for sterilizing or disinfecting an object comprising:

a housing having walls defining a chamber within the housing for receiving at least a portion of the object;

an ultraviolet light source disposed within the housing so that ultraviolet light emitted from the ultraviolet light source may enter the chamber;

wherein when at least a portion of the object is placed within the chamber, a seal is formed between at least part of the object and the walls to substantially contain ultraviolet light emitted from the ultraviolet light source within the housing; and a lockout device that disables operation of the light source until the portion of the object has been placed within the chamber and the seal is substantially complete;

wherein upon substantial completion of the seal, the ultraviolet light source emits a flash of ultraviolet light.

* * * * *